United States Patent

Kitamura et al.

[11] Patent Number: 5,919,968
[45] Date of Patent: Jul. 6, 1999

[54] PROCESS FOR PREPARING ORGANIC PENTAVALENT PHOSPHORUS COMPOUNDS

[75] Inventors: Kozo Kitamura, Osaka; Tsuyoshi Kihara, Sakai; Yoshinori Tanaka, Habikino; Yoshimi Yano, Higashiosaka, all of Japan

[73] Assignee: Daihachi Chemical Industry Co., Ltd., Osaka, Japan

[21] Appl. No.: 08/966,651

[22] Filed: Nov. 10, 1997

Related U.S. Application Data

[63] Continuation-in-part of application No. 08/904,629, Aug. 1, 1997, abandoned.

[30] Foreign Application Priority Data

Nov. 21, 1996 [JP] Japan .................................. 8-310966
Jul. 30, 1997 [JP] Japan .................................. 9-204687
Oct. 1, 1997 [JP] Japan .................................. 9-268694

[51] Int. Cl.$^6$ ............................................. C07F 9/09
[52] U.S. Cl. ....................... 558/122; 564/12; 564/13; 568/12; 568/14
[58] Field of Search ................................ 558/122

[56] References Cited

U.S. PATENT DOCUMENTS

| | | |
|---|---|---|
| 2,851,476 | 9/1958 | Hechenbleikner . |
| 3,027,395 | 3/1962 | Sharp et al. . |
| 3,042,698 | 7/1962 | Birum . |
| 3,042,700 | 7/1962 | Birum . |
| 3,277,217 | 10/1966 | Nehmsmann et al. . |
| 3,484,491 | 12/1969 | Ito et al. . |
| 4,450,147 | 5/1984 | Elsner et al. . |

FOREIGN PATENT DOCUMENTS

| | | |
|---|---|---|
| 51-6250 | 1/1976 | Japan . |
| 1097805 | 1/1968 | United Kingdom . |

OTHER PUBLICATIONS

Derwent Abstract No. 78–83623, published Feb. 1, 1978.
Patent Abstracts of Japan, vol. 12, No. 344 (C–528), published Sep. 16, 1988.
Sugimoto et al., "Ferric Chloride Induced Activation of Hydrogen Peroxide for the Epoxidation of Alkenes and Monoxygenation of Organic Substrates in Acetonitrile", *Journal of Organic Chemistry*, vol. 50, No. 10, pp. 1784–86 (1985).
Barton, Derek H.R. et al. "Catalysis of the Oxidation of Triphenylphosphine and of Trimethyl Phosphite by Hydrogen Peroxidein the Presence of Fe(III) Compounds" Tetrahedron Letters 38(10), 1711–12 (1997).
"Assay System for Chlorine Ion Using a Silver Nitrate Standard Liquid", *Experiments for Analytical Chemistry* (1964).
CADOGAN, "Oxidation of Tervalent Organic Compounds of Phosphorus", *Quart. Rev.*, 16, pp. 208–239 (1962).

*Primary Examiner*—Michael G. Ambrose
*Attorney, Agent, or Firm*—Greenblum & Bernstein, P.L.C.

[57] ABSTRACT

A process for preparing an organic pentavalent phosphorus compound comprising oxidizing an organic trivalent phosphorus compound with an aqueous hydrogen peroxide solution in the presence of an inorganic or organic base at a temperature of 0° C. to 50° C. to obtain the corresponding organic pentavalent phosphorus compound.

19 Claims, 1 Drawing Sheet

PROCESS FOR PREPARING ORGANIC PENTAVALENT PHOSPHORUS COMPOUNDS

CROSS-REFERENCE TO RELATED APPLICATIONS

This application is a continuation-in-part of application Ser. No. 08/904,629, filed on Aug. 1, 1997, now abandoned.

Also this application is related to Japanese applications No. Hei 8(1996)-310966, filed on Nov. 21, 1996, No. Hei 9(1997)-204687, filed on Jul. 30, 1997 and Hei 9(1997)-268694, filed on Oct. 1, 1997, whose priorities are claimed under 35 USC § 119, the disclosure of which is incorporated by reference in its entirety.

BACKGROUND OF THE INVENTION

1. Field of the Invention

The present invention relates to a process for preparing organic pentavalent phosphorus compounds, more particularly, a process for oxidizing organic trivalent phosphorus compounds using an aqueous hydrogen peroxide solution, without causing hydrolysis of the phosphorus compounds, to obtain the corresponding organic pentavalent phosphorus compounds.

2. Description of Related Art

The organic pentavalent phosphorus compounds typified by haloalkyl phosphate/polyphosphonates, trialkyl phosphates, triaryl phosphates, trialkyl phosphonates, triaryl phosphonates and trialkyl phosphinates are generally used as plasticizers, flame-retardants, stabilizers for synthetic resins, lubricants or metal-extracting reagents or the like. The organic pentavalent phosphorus compounds are usually obtained by oxidizing the corresponding organic trivalent phosphorous compounds (see Quat. Rev., 16, 208–239, 1962).

For example, the reaction of (n+1) moles of phosphorus trichloride with (2n+3) moles of an alkylene oxide followed by reacting with n moles of an aliphatic aldehyde or ketone is represented by the following scheme:

First Reaction

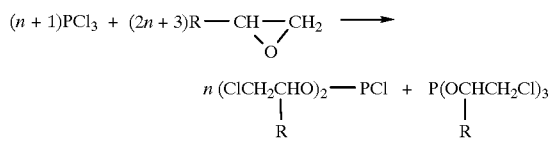

Second Reaction

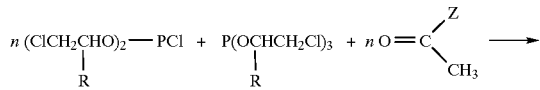

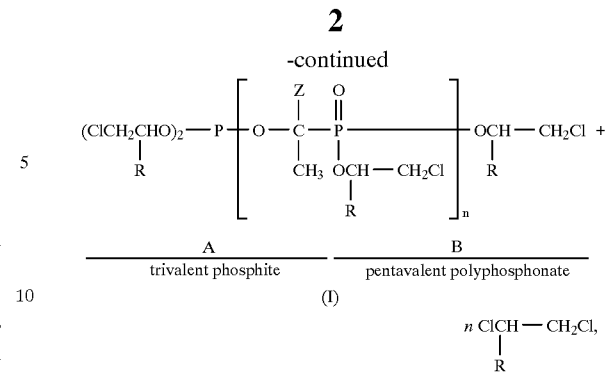

wherein R and Z are, the same or different, a hydrogen atom or a lower alkyl group, and n is an integer from 0 to 10.

The obtained compound of the formula (I) is a (trivalent) phosphite/(pentavalent)polyphosphonate. The compound can be oxidized using various oxidizing agents to give a (pentavalent) phosphate/(pentavalent) polyphosphonate of the following formula (IV):

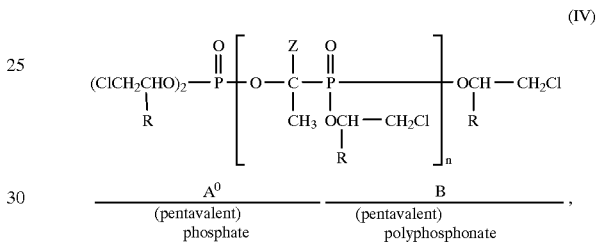

wherein R and Z have the same meanings as defined for the formula (I).

The compound of the formula (I) consists of a structural part A of a trivalent phosphite and a structural part B of a pentavalent polyphosphonate. The structural part B having a P—C (phosphorus—carbon) bond can hardly be hydrolyzed and exhibits good heat resistance. On the other hand, the structural part A containing trivalent phosphorus can easily be hydrolyzed and is poor in heat resistance. Therefore, the compound of the formula (I) is hardly used as a flame retardant or a modifier for synthetic resins and polyurethane foams. In order to improve the hydrolytic resistance and heat resistance, trivalent phosphorus must be oxidized to pentavalent phosphorus.

A trivalent phosphorus compound represented by the formula (III):

$$(R^1O)_{3-a}P\text{-}R^2_a, \quad (III)$$

wherein $R^1$ and $R^2$ are, the same or different, an alkyl or haloalkyl group having 1 to 18 carbon atom(s), or an aryl group having 6 to 10 carbon atoms, and a is an integer from 0 to 2, consists of structural parts C and D as shown in the following formula when a=1, for example:

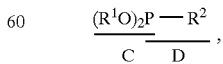

wherein $R^1$ and $R^2$ have the same meanings as defined in the formula (III).

The structural part D of >P—$R^2$ has a >P—C (phosphorus-carbon) band and is hardly hydrolyzed. On the other hand, the structural part C of $(R^1O)_2P-$ is easily hydrolyzed. Accordingly, the compound of the formula (III) must also be stabilized by oxidation.

However, the aforesaid organic trivalent phosphorus compounds are hydrolyzed when oxidized only using an aqueous hydrogen peroxide solution as an oxidizing agent.

Oxidative methods of the organic trivalent phosphorus compounds are described in U.S. Pat. Nos. 3,027,395, 3,042,698, 3,042,700, and Japanese Unexamined Patent Publication No. Sho 51(1976)-6250 wherein propylene trimer hydroperoxide, sulfur, oxygen/ozone, and chlorine are used as an oxidizing agent, respectively. However, none of the above references disclose an oxidation method using an aqueous hydrogen peroxide solution as an oxidizing agent.

SUMMARY OF THE INVENTION

The present inventors have made keen study to solve the aforesaid problems finally to achieve the present invention.

The present invention provide a process for preparing an organic pentavalent phosphorus compound comprising oxidizing an organic trivalent phosphorus compound with an aqueous hydrogen peroxide solution in the presence of an inorganic or organic base at a temperature of about 0° C. to about 50° C. to obtain the corresponding organic pentavalent phosphorus compound.

DESCRIPTION OF THE PREFERRED EMBODIMENTS

Figure 1:
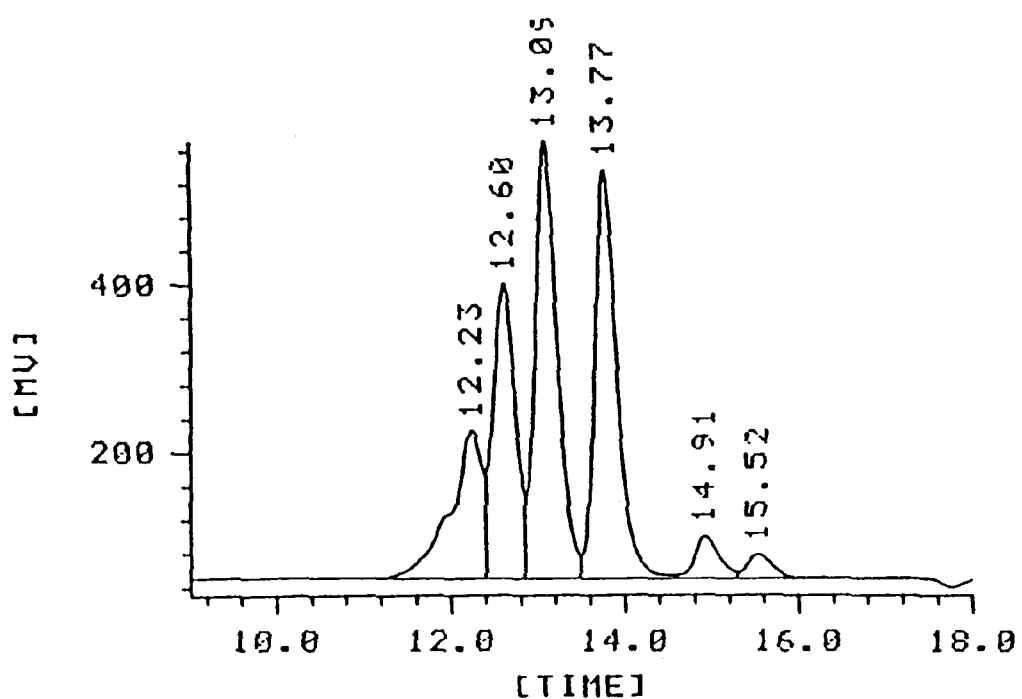
FIG. 1 is a gel permeation chromatography (GPC) chart of an organic pentavalent phosphorus compound obtained in Example 4.

The organic trivalent phosphorus compounds used in the present invention are compounds having at least one trivalent phosphorus atom to which three organic groups are bonded. Specifically, the organic trivalent phosphorus compounds used in the present invention are preferably selected from the compounds of the formula (I):

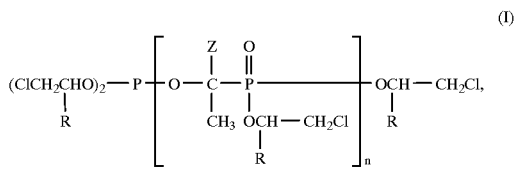

wherein R and Z are, the same or different, a hydrogen atom or a lower alkyl group, and n is an integer from 1 to 10, those of the formula (II):

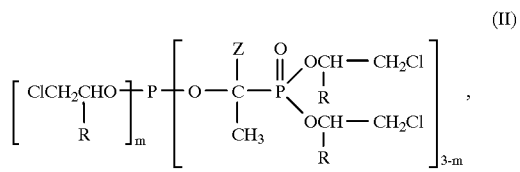

wherein R and Z have the same meanings as defined in the formula (I), and m is 0 or 1, and those of the formula (III):

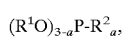

wherein $R^1$ and $R^2$ are, the same or different, an alkyl or haloalkyl group having 1 to 18 carbon atom(s) or an aryl group having 6 to 10 carbon atoms, and a is an integer from 0 to 2.

The lower alkyl group of the substituents R and Z in the above formulae (I) and (II) is a straight-chain or branched alkyl group having 1 to 4 carbon atom(s) including methyl, ethyl, n-propyl, iso-propyl, n-butyl, iso-butyl and sec-butyl. The substituent R is preferably a hydrogen atom or methyl group, and the substituent Z is preferably hydrogen atom, a methyl or ethyl group.

The alkyl group having 1 to 18 carbon atom(s) of the substituents $R^1$ and $R^2$ in the above formula (III) is a straight-chain or branched chain alkyl group, or a cycloalkyl group. Specific examples thereof are a lower alkyl group having 1 to 6 carbon atom(s) including methyl ethyl, n-propyl, iso-propyl, n-butyl, iso-butyl, sec-butyl, n-pentyl, iso-pentyl, hexyl, a higher alkyl group having 7 to 18 carbon atoms including heptyl, octyl, nonyl, decyl, undecyl, dodecyl, tridecyl, tetradecyl, pentadecyl, hexadecyl, heptadecyl and octadecyl; methylhexyl, methylheptyl, methyloctyl, methylnonyl, methyldecyl, methylundecyl, methyldodecyl, methyltridecyl, methyltetradecyl, methylpentadecyl, methylhexadecyl and methylheptadecyl; dimethylhexyl, dimethylheptyl, dimethyloctyl, dimethylnonyl, dimethyldecyl, dimethylundecyl, dimethyldodecyl, dimethyltridecyl, dimethyltetradecyl, dimethylpentadecyl and dimethylhexadecyl; 2-ethylhexyl, ethylheptyl, ethyloctyl, ethylnonyl, ethyldecyl, ethylundecyl, ethyldodecyl, ethyltridecyl, ethyltetradecyl, ethylpentadecyl and ethylhexadecyl, and a cycloalkyl group including cyclobutyl and cyclohexyl, among which n-butyl, 2-ethylhexyl and cyclohexyl are preferred.

The haloalkyl group having 1 to 18 carbon atom(s) is a straight-chain or branched haloalkyl group including the above-mentioned alkyl groups whose hydrogen atoms are optionally substituted with halogen atoms. The halogen atoms include fluorine, chlorine, bromine and iodine, among which chlorine is preferred. Examples of the haloalkyl groups are chloroethyl and chloropropyl.

Examples of the aryl group having 6 to 10 carbon atoms are phenyl, tolyl, xylyl, cumenyl, mesityl, naphthyl, dimethylphenyl and trimethylphenyl, among which phenyl and tolyl are preferred.

Examples of the organic trivalent phosphorus compounds of the formula (III) are triethyl phosphite, tributyl phosphite, trioctyl phosphite, tridecyl phosphite, tricyclohexyl phosphite, tristearyl phosphite, triphenyl phosphite, tricresyl phosphite, tri(2,6-dimethylphenyl) phosphite, tri(2,4,6-trimethylphenyl)phosphite, tri(nonylphenyl)phosphite, tris (chloroethyl)phosphite, tris(chloropropyl)phosphite and tris (dichloropropyl) phosphite in the case of a=0, organic phosphonites in the case of a=1, and organic phosphinites in the case of a=2.

As the organic trivalent phosphorus compound, usable is a reaction mixture obtained by reacting phosphorus trichloride with an alkylene oxide and then with an aliphatic aldehyde or ketone. The reaction mixture does not particularly need purification, but may contain reaction byproducts.

Examples of the inorganic bases used in the present invention are hydroxides of alkaline metals such as lithium hydroxide, sodium hydroxide and potassium hydroxide, carbonates of alkaline metals such as sodium carbonate, hydrogencarbonate of alkaline metals such as sodium hydrogencarbonate, and ammonia. The inorganic bases may be used in the form of aqueous solution. Among them, aqueous solution of sodium hydroxide is preferred. The concentration thereof is not particularly limited, but may be preferably about 10% to about 40%, more preferably about 20% to about 30%.

Examples of the organic bases used in the present invention are aliphatic amines such as dimethylamine, diethylamine, trimethylamine, triethylamine and tributylamine, aromatic amines such as dimethylaniline, and aromatic heterocyclic bases such as pyridine and picoline, among which triethylamine and pyridine are preferred.

The above-described inorganic and organic bases may be used as a mixture thereof.

The above-described inorganic and organic bases may be preferably used in such an amount as the inorganic and organic bases can make alkaline a reaction mixture resulting from the oxidation reaction with an aqueous hydrogen peroxide solution. Specifically, the reaction mixture may preferably be adjusted to pH8 to 12. Surprisingly, under such a condition, the hydrolysis of the organic trivalent phosphorus compound can be inhibited, the decomposition of hydrogen peroxide is promoted, and the oxidation reaction can be completed.

The aforesaid bases may be added before the beginning of the oxidation reaction or at the same time as aqueous solution of hydrogen peroxide is added.

The aqueous hydrogen peroxide solution used in the present invention may be commercially available. The concentration thereof is not particularly limited, but is preferably about 3% to about 50%, more preferably about 20% to about 35%. When the concentration is below 3%, the reaction efficiency is poor. On the other hand, an aqueous hydrogen peroxide solution of a concentration higher than 50% is not easily available industrially.

The oxidation reaction of the present invention may be carried out in the presence of a solvent. As the solvent, usable is water and an organic solvent inert to the reaction. Examples of the organic solvents are aliphatic hydrocarbons such as hexane and cyclohexane, aromatic hydrocarbons such as benzene and toluene, and organic halogen compounds such as chloroform and dichloroethane, among which benzene and dichloroethane are preferred. The organic solvent may be one which has been used for preparing the organic trivalent phosphorus compound. In other words, a reaction mixture at the preparation of the organic trivalent phosphorus compound may be used as it is.

The reaction may preferably be carried out at a temperature below about 50° C., for example, 0° C. to 50° C., preferably 10° C. to 30° C. Since the reaction of the present invention is strongly exothermic, the reaction system may be cooled to the above-mentioned temperature range, if necessary. The reaction time varies mainly depending on the concentration of the aqueous hydrogen peroxide solution, but is normally 3 to 7 hours.

After the oxidation reaction is completed, a reaction mixture may be subjected to an ordinary after-treatment for organic phosphorus compounds to separate the desired organic pentavalent phosphorus compound. Specifically, the reaction mixture may be subjected to water washing (or warm water washing), neutralization, water washing (or warm water washing), recovery of by-products such as a halogenated alkyl, and dehydration under reduced pressure. By the above-described process, the desired organic pentavalent phosphorus compound can be obtained in a yield of about 80% to about 95%.

The oxidation process of the present invention can be used for oxidizing oligomers and polymers of phosphites, phosphonites and phosphinites. Further, the oxidation process of the present invention can be used for oxidizing organic trivalent phosphorus compounds as intermediates in preparation of agricultural chemicals and pharmaceuticals.

EXAMPLES

The present invention will hereinafter be described in details by way of examples, which should not be understood to limit the scope of the invention.

Intermediate reaction mixture and desired organic pentavalent phosphorus compounds obtained by the examples were evaluated by the following methods.

Concentration of Active Chlorine

Concentration (%) of active chlorine in the reaction mixture in the first reaction for preparing an organic trivalent phosphorus compound was determined according to "Assay System for Chlorine Ion Using a Silver Nitrate Standard Liquid" described in "Experiments for Analytical Chemistry" (published by Kagakudojin in Japan) to ensure the completion of the first reaction.

Acid Value

Acid value (KOH mg/g) of the reaction mixture after the second reaction for preparing the organic trivalent phosphorus compound and of the end product was determined according to "K0070-1966 of JIS (Japanese Industrial Standard)" [using BTB (Bromothymol Blue) as an indicator].

Concentration of Phosphorus in the Phosphite Portion (referred to as PI hereafter for short)

PI (%) was determined for the obtained organic trivalent phosphorus compound by titration of iodine consumed by the phosphite using sodium thiosulfate.

Yield

Yield of the end product of the organic pentavalent phosphorus compound, was calculated based on a theoretical yield from assumed quantitative reaction of the starting material, i.e., the phosphorus trichloride, with the alkylene oxide.

Appearance, Specific Gravity, Viscosity

Appearance of the end product of the organic pentavalent phosphorus compound, was visually observed, and the specific gravity (at 20° C.) and viscosity (cp at 25° C.) thereof were determined according to "K0061 of JIS" and "K2283 of JIS," respectively.

Composition

Composition of the end product of the organic pentavalent phosphorus compound was determined by gel permeation chromatography (GPC) using HLC-8020 manufactured by Tosoh Corporation, Japan.

Phosphorus Content

Phosphorus content (P %) in the end product of the organic pentavalent phosphorus compound was obtained from absorbance of the product and the calibration curve of phosphorus standard liquids. The absorbance was determined by adding nitric acid and perchloric acid to the product, decomposing with heat, diluting with distilled water, adding an appropriate amount of nitric acid, a solution of ammonium vanadate and a solution of ammonium molybdate to develop color, and measuring the absorbance using a spectrophotometer.

Chlorine Content

Chlorine content (Cl %) in the end product of the organic pentavalent phosphorus compound was obtained by thermally decomposing the end product containing chloroalkyl using n-butanol/metallic sodium, and potentiometrically titrating the liberated chlorine using an aqueous silver nitrate solution.

Example 1

An organic trivalent phosphorus compound was synthesized by the following first and second reactions.

First Reaction

One hundred thirty-seven point five grams (137.5 g, 1.0 mol) of phosphorus trichloride, 50.0 g of dichloroethane and 0.28 g of triethylamine (0.20%/PCl$_3$) were put in a 500 ml flask provided with a stirrer, a thermometer, a tube for blowing an alkylene oxide and condenser, and were cooled to 10° C. in a ice-water bath. Then, 106.0 g (2.4 mols) of ethylene oxide gas is blown in from a bomb through a flowmeter. The reaction temperature was 10° to 30° C. and the reaction time was 4 hours. The concentration of active chlorine in the reaction mixture was 8.2% (the theoretical value thereof was 8.6%).

Second Reaction

Thirty-nine point three grams (39.3 g, 0.68 mols) of acetone was added to the reaction mixture of the first reaction by a dropping funnel at 30 to 50° C. in 30 minutes. The reaction temperature was then raised gradually to 80 to 90° C., and the reaction mixture was allowed to react for 4 hours. The acid value of the reaction mixture was 2, the PI is 4.38% (the calculated value was 4.57%).

The obtained organic trivalent phosphorus compound was oxidized by the following third reaction to produce an organic pentavalent phosphorus compound.

Third Reaction (Oxidization)

Seven grams (7 g) of a 30% aqueous sodium hydroxide solution was added to the reaction mixture of the second reaction by a dropping funnel at 10 to 20° C. in 20 minutes. The pH of the resulting reaction mixture was 10.5. Then, 43.8 g (0.45 mols) of a 35% aqueous hydrogen peroxide solution was added to the reaction mixture at 10 to 30° C. in 4 hours. While adding the aqueous hydrogen peroxide solution, a 30% aqueous sodium hydroxide solution was added to maintain the pH of the reaction mixture at 8.5 to 10.5. The total used amount of the 35% aqueous sodium hydroxide solution was 14.1 g. After completing the addition of the aqueous hydrogen peroxide solution, the reaction mixture was kept at 30 to 40° C. for 2 hours.

After-treatment

To the reaction mixture resulting from the third reaction, 4.3 g of a 30% aqueous sodium hydroxide solution was added. The resulting reaction mixture was stirred at 50° C. for an hour, and then was left at rest in a separatory funnel to be separated into an aqueous phase and an organic phase.

The obtained organic phase was washed twice with 100 ml of warm water (40 to 50° C.) and distilled at 120° C. under a reduced pressure of 30 to 80 mmHg. The remaining oily product weighed 201 g (the yield was 89.0%), the acid value was 0.40, and the PI was 0%. The composition and quality of the product are shown in Table 1.

Comparative Example 1

The same reactions as in Example 1 were carried out except that aqueous sodium hydroxide solution was not used in the third reaction. In third reaction, intense hydrolysis took place. The acid value of the reaction mixture after the addition of aqueous hydrogen peroxide solution was 14. Because of the intense hydrolysis of the product, the after-treatment was not carried out.

Example 2

The following materials underwent the same reactions as those in Example 1:

| Materials in the first reaction | |
|---|---|
| Phosphorus trichloride | 137.5 g (1.0 mol) |
| Triethylamine | 0.3 g (0.2%/PCl$_3$) |
| Ethylene oxide | 98.1 g (2.23 mols) |
| Material in the second reaction | |
| Acetaldehyde | 39.0 g (0.89 mols) |
| Materials in the third reaction | |
| 35% aqueous hydrogen peroxide solution | 24.6 g (0.25 mols) |
| 25% aqueous sodium hydroxide solution | 14.1 g |

The concentration of active chlorine after the first reaction was 11.3% (the theoretical value was 11.6%). After the second reaction, the acid value was 1.8, and the PI was 2.60%. The obtained product was 167 g in weight (the yield was 84.8%), the acid value was 0.30, and the PI was 0%. The composition and quality of the product are shown in Table 1.

Example 3

The following materials underwent the same reactions as those in Example 1:

| Materials in the first reaction | |
|---|---|
| Phosphorus trichloride | 137.5 g (1.0 mol) |
| Triethylamine | 0.3 g |
| Propylene oxide | 145.0 g (2.5 mols) |
| Material in the second reaction | |
| Acetaldehyde | 25.3 g (0.58 mols) |
| Materials in the third reaction | |
| 35% aqueous hydrogen peroxide solution | 53.4 g (0.55 mols) |
| 25% aqueous sodium hydroxide solution | 18.5 g |

The concentration of active chlorine after the first reaction was 5.9% (the theoretical value was 6.27%). After the second reaction, the acid value was 2.2, and the PI was 5.0%. The obtained product was 214 g in weight (the yield was 83.5%), the acid value was 0.25, and the PI was 0%. The composition and quality of the product are shown in Table 1.

Example 4

| Materials in the first reaction | |
|---|---|
| (1) Phosphorus trichloride | 137.5 g (1.0 mol) |
| Benzene | 90.0 g |
| Triethylamine | 0.3 g |

-continued

| | |
|---|---|
| Ethylene oxide | 141.3 g (3.2 mols) |
| (2) Phosphorus trichloride | 68.4 g (0.5 mol) |
| Ethylene oxide | 23.0 g (0.977 mols) |
| Material in the second reaction | |
| Acetone | 62.0 g (1.069 mols) |
| Materials in the third reaction | |
| 35% aqueous hydrogen peroxide solution | 69.9 g (0.719 mols) |
| Triethylamine | 10.3 g (5%/PCl$_3$) |

The above-mentioned materials underwent the same reactions as those in Example 1 except the following:

The first reaction (1) was carried out under the same condition as in Example 1. Then, benzene was recovered at 90 to 100° C. under a reduced pressure of 100 mmHg or below. A reaction mixture containing 1 mol (the theorical value) of tris(chloroethyl)phosphite was obtained.

In the first reaction (2), phosphorus trichloride was added to the reaction mixture of the first reaction (1). The resulting reaction mixture was then reacted with ethylene oxide to synthesize 0.5 mols (the theorical value) of bis(chloroethyl) phosphorochloridate. The concentration of active chlorine in the reaction mixture was 8.3% (the theoretical value was 8.58%).

In the second reaction, acetone was added to the reaction mixture containing 1 mol of tris(chloroethyl)phosphite and 0.5 mols of bis(chloroethyl)phosphorochloridate of the first reaction (1) and the first reaction (2), respectively. The resulting reaction mixture was allowed to react at 80 to 100° C. for 5 hours. The acid value was 2.4 and the PI was 4.5%, after the reaction.

In the third reaction, the reaction mixture resulting from the second reaction was cooled to 10° C. Then, triethylamine was added. An 35% aqueous hydrogen peroxide solution was then added at 10 to 30° C. in 2 hours. The pH of the reaction mixture was 10.8 immediately after the addition of the 35% aqueous hydrogen peroxide solution, and was 8.5 after the completion of the addition. The reaction mixture was further allowed to react at 30 to 35° C. for 2 hours. The reaction mixture was washed twice with 200 ml of water. Then dichloroethane and water were distilled off under a reduced pressure of 10 to 50 mmHg. The obtained product was 294 g in weight (the yield was 90.0%), the acid value was 0.73, and the PI was 0%. The composition and quality of the product are shown in Table 1.

TABLE 1

| | EXAMPLE 1 | EXAMPLE 2 | EXAMPLE 3 | EXAMPLE 4 |
|---|---|---|---|---|
| Composition of Products n (%) | | | | |
| unknown | 1.1 | 0.1 | 0.1 | 2.0 |
| 0 | 14.5 | 0.2 | 21.4 | 3.3 |
| 1 | 59.9 | 8.1 | 45.3 | 23.4 |
| 2 | 19.0 | 16.0 | 24.8 | 30.7 |
| 3 | 4.7 | 18.9 | 8.4 | 20.6 |
| 4 | 0.9 | 18.0 | | 15.0 |
| 5 | | 37.1 | | |
| R | H | H | CH$_3$ | H |
| Z | CH$_3$ | H | H | CH$_3$ |
| Yield (%) | 89.0 | 84.8 | 83.5 | 90.0 |

TABLE 1-continued

| | EXAMPLE 1 | EXAMPLE 2 | EXAMPLE 3 | EXAMPLE 4 |
|---|---|---|---|---|
| Quality | | | | |
| Appearance | Transparent Liquid | Transparent Liquid | Transparent Liquid | Transparent Liquid |
| Specific Gravity 20/20° C. | 1.41 | 1.45 | 1.31 | 1.40 |
| Acid Value KOH mg/g | 0.40 | 0.30 | 0.25 | 0.73 |
| Viscosity 25° C. cp | 750 | 61,400 | 1,516 | 3,521 |
| Elements | | | | |
| P % | 13.2 | 15.9 | 12.0 | 13.8 |
| Cl % | 27.8 | 25.2 | 27.1 | 26.7 |
| PI % | 0 | 0 | 0 | 0 |

The reference characters n, R, and Z in the composition of the products correspond to like characters in Formula (I). The composition was determined from a GPC chart.

FIG. 1 is the GPC chart of the product obtained in Example 4. The chart shows that compounds wherein n=5 or more are not separated, showing a shoulder peak.

Example 5

A commercial available triphenyl phosphite (TPI) (JP360 produced by Johoku Chemical Co., Ltd. in Japan) was oxidized by the method of the present invention.

The same flask as used in Example 1 was employed except that a dropping funnel was substituted for the tube for blowing the alkylene oxide. Into this flask, 310 g (1 mol) of TPI, 100 g of benzene as a solvent, 16 g of triethylamine (5%/TPI) were put and cooled to 10° C. Then, 107 g (1.10 mols) of a 35% aqueous hydrogen peroxide solution were added at 10 to 15° C. in an hour. The pH of the reaction mixture during the addition of the 35% aqueous hydrogen peroxide solution was 8 to 10. Then, the reaction mixture was allowed to react at 10 to 15° C. for 2 hours and washed with the same amount of warm water (40 to 50° C.). After washing, the reaction mixture was neutralized with alkali, further washed with the same amount of warm water (40 to 50° C.), and distilled under a reduced pressure of 3 mmHg.

The main fraction distilled at 210 to 220° C. under 3 mmHg weighed 264 g (the yield was 81.0%). This product was white powder having a melting point of 48.4° C. The acid value was 0.1 and the P% was 10.6%.

Comparative Example 2

The following materials was subjected to the same reaction as described in Example 5 except that triethylamine was not employed. The pH during the reaction was 1 to 4. The acid value of the reaction mixture was 10.8. Since hydrolysis occurred and the acid value was high, the after-treatment was not carried out.

| | |
|---|---|
| Materials | |
| TPI (reagent grade) | 310 g (1.0 mol) |
| Solvent Benzene | 100 g |
| 35% aqueous solution of hydrogen peroxide (10% excess over a theoretical amount) | 57 g |

Example 6

Synthesis of tributyl phosphate

In a one-liter four-necked flask provided with a stirrer, thermometer, dropping funnel and condenser, 122 g (1.65 mols) of butanol, 130 g (1.65 mols) of pyridine as a trapping agent for hydrochloric acid, and 200 g of benzene as a solvent were put. To this mixture, 69 g (0.5 mols) of phosphorus trichloride was added at 5° C. or below in 40 minutes. Then, the resulting mixture was allowed to react at 5° C. or below for 2 hours. Then the reaction mixture was cooled. Precipitated hydrochloride of pyridine was filtered off, and washed with 50 g of benzene to obtain 365 g of filtrate. Gas chromatography showed that tributyl phosphite was generated in the filtrate.

The obtained filtrate was put in the same flask as described above, and 5 g of pyridine was added. Then, 54 g (0.55 mols) of a 35% aqueous hydrogen peroxide solution were added by the dropping funnel at 5° C. or below in 40 minutes. The reaction during adding the aqueous hydrogen peroxide solution was exothermic. The reaction mixture was allowed to react further for an hour, and then put into a separatory funnel. The reaction mixture was subjected to after-treatment of water washing, neutralization with a 5% aqueous sodium hydroxide solution and recovery of benzene, and then distilled under reduced pressure.

The obtained main component weighed 111 g (the yield was 83.0%). This product was transparent liquid having a specific gravity of 0.978 (20/20° C.) and a boiling point of 145 to 150° C./3 mmHg. Gas chromatography showed that the main component was tributyl phosphate.

According to the present invention, the organic trivalent phosphorus compound is oxidized with an aqueous hydrogen peroxide solution at a temperature of 0 to 50° C. in the presence of an organic or inorganic base to produce the corresponding organic pentavalent phosphorus compound. Thus, hydrolysis of the organic trivalent phosphorus compound can be inhibited, and the oxidation smoothly proceeds. The method of the present invention is industrially advantageous because the aqueous hydrogen peroxide solution used as an oxidant is industrially available at low cost, the reaction process is simple and waste water disposal is easy. Furthermore, the organic pentavalent phosphorus compound can be produced in a high yield of 80 to 95% according to the present invention.

What is claimed is:

1. A process for preparing an organic pentavalent phosphorus compound, comprising:

oxidizing organic trivalent phosphorus compound with aqueous hydrogen peroxide solution in the presence of at least one base at a temperature of 0° C. to 50° C. to organic pentavalent phosphorus compound, wherein the organic trivalent phosphorus compound comprises a reaction mixture obtained by reacting phosphorus trichloride with alkylene oxide and then with one of aliphatic aldehyde and aliphatic ketone.

2. The process of claim 1, wherein the at least one base comprises at least one inorganic base selected from the group consisting of lithium hydroxide, sodium hydroxide, potassium hydroxide, sodium carbonate, sodium hydrogencarbonate, and ammonia, and at least one organic base selected from the group consisting of dimethylamine, diethylamine, trimethylamine, triethylamine, tributylamine, dimethylaniline, pyridine, and picoline.

3. The process of claim 1, wherein the at least one base comprises at least one inorganic base selected from the group consisting of lithium hydroxide, sodium hydroxide, potassium hydroxide, sodium carbonate, sodium hydrogencarbonate, and ammonia.

4. The process of claim 1, wherein the at least one base comprises at least one organic base selected from the group consisting of dimethylamine, diethylamine, trimethylamine, triethylamine, tributylamine, dimethylaniline, pyridine, and picoline.

5. The process of claim 1, wherein the at least one base comprises inorganic base comprising aqueous sodium hydroxide solution having a concentration of 10 to 40%.

6. The process of claim 1, wherein the at least one base comprises organic base comprising triethylamine.

7. The process of claim 1, wherein the at least one base comprises organic base comprising pyridine.

8. The process of claim 1, wherein the at least one base is used in an amount to maintain a pH of 8 to 12.

9. The process of claim 1, wherein the alkylene oxide comprises ethylene oxide.

10. The process of claim 1, wherein the alkylene oxide comprises propylene oxide.

11. The process of claim 1, wherein the one of aliphatic aldehyde and aliphatic ketone comprises acetaldehyde.

12. The process of claim 1, wherein the one of aliphatic aldehyde and aliphatic ketone comprises acetone.

13. The process of claim 1, wherein the aqueous hydrogen peroxide solution has a concentration of 3 to 50%.

14. The process of claim 1, wherein the aqueous hydrogen peroxide solution has a concentration of 20 to 35%.

15. The process of claim 1, wherein the temperature is 10 to 30° C.

16. The process of claim 1, wherein the oxidation is carried out in a solvent comprising benzene.

17. The process of claim 1, wherein the oxidation is carried out in a solvent comprising dichloroethane.

18. The process of claim 1, wherein the organic trivalent phosphorus compound is selected from the group consisting of formula (I) and formula (II), wherein formula (I) follows:

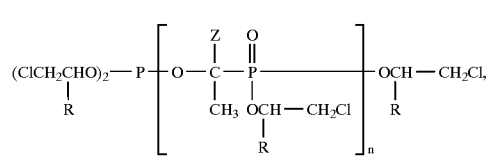

wherein R and Z are, the same or different, hydrogen or lower alkyl group, and n is an integer from 0 to 10; and wherein formula (II) follows:

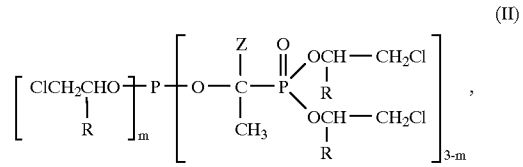

wherein R and Z have the same meanings as defined with respect to formula (I), and m is one of 0 and 1.

19. The process of claim 18, wherein R in formulas (I) and (II) is selected from hydrogen and methyl group, and Z is selected from the group consisting of hydrogen, methyl group, and ethyl group.

* * * * *